(12) United States Patent
Hess et al.

(10) Patent No.: US 7,820,373 B2
(45) Date of Patent: Oct. 26, 2010

(54) NATRIURETIC PEPTIDES AND PLACENTA GROWTH FACTOR LEVELS FOR RISK STRATIFICATION

(75) Inventors: Georg Hess, Mainz (DE); Andrea Horsch, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/186,958

(22) Filed: Aug. 6, 2008

(65) Prior Publication Data

US 2009/0047697 A1 Feb. 19, 2009

Related U.S. Application Data

(63) Continuation of application No. PCT/EP2007/051027, filed on Feb. 2, 2007.

(30) Foreign Application Priority Data

Feb. 6, 2006 (EP) .................................. 06101338

(51) Int. Cl.
*C12Q 1/00* (2006.01)
(52) U.S. Cl. .......................................... 435/4; 600/483
(58) Field of Classification Search ..................... 435/4; 600/483
See application file for complete search history.

(56) References Cited

U.S. PATENT DOCUMENTS

| | | | |
|---|---|---|---|
| 2004/0243010 A1* | 12/2004 | Zoghbi et al. | ................ 600/508 |
| 2007/0042438 A1* | 2/2007 | Zeiher et al. | .................. 435/7.5 |
| 2009/0081702 A1* | 3/2009 | Hess et al. | .................... 435/7.4 |

OTHER PUBLICATIONS

Weber M. et al. N-Terminal B-Type Natriuretic Peptide Predicts Extent of Coronary Artery Disease . . . American Heart Journal 148:612-620, 2004.*
Sabatine M. et al. Acute Changes in Circulating Natriuretic Peptide Levels in Relation to Myocardial Ischemia. J of the American College of Cardiology 44(10)1988-95, 2004.*
Foote R. et al. Detection of Exercise Induced Ischemia by Changes in B-Type Natriuretic Peptides. J of the American College of Cardiology 44(10)1980-7, 2004.*

* cited by examiner

*Primary Examiner*—Ralph Gitomer
(74) *Attorney, Agent, or Firm*—Marilyn L. Amick; Roche Diagnostics Operations, Inc.

(57) ABSTRACT

The present invention relates to a method for determining a risk whether an individual will suffer from a cardiovascular adverse event as a consequence of cardiac stress testing, comprising the steps of (a) measuring, preferably in vitro, the level of placenta growth factor, wherein (b) if the level of the placenta growth factor is at least increased, then the individual is at least at risk of suffering from an adverse event as a consequence of cardiac stress testing. In a further embodiment, additionally another marker is measured, particularly a natriuretic peptide, most particularly NT-proBNP. The present invention allows to stratify patients according to the environment and conditions under which cardiac stress testing should be carried out.

9 Claims, No Drawings

US 7,820,373 B2

NATRIURETIC PEPTIDES AND PLACENTA GROWTH FACTOR LEVELS FOR RISK STRATIFICATION

RELATED APPLICATIONS

This application is a continuation of PCT/EP2007/051027 filed Feb. 2, 2007 and claims priority to EP 06101338.9 filed Feb. 6, 2006.

FIELD OF THE INVENTION

The present invention relates to methods and uses for risk stratification of individuals elected for cardiac stress testing.

BACKGROUND

Cardiac stress testing is an important and widely used test for diagnosis of cardiovascular dysfunctions, particularly coronary heart disease. Cardiac stress testing is carried out to investigate how the cardiovascular system, particularly the heart, performs during exercise. In a typical example, the individual is asked to walk on a treadmill or to ride a stationary bike while diagnostic parameters such as an electrocardiogram or an echocardiogram are recorded. The exercise can also be simulated by administering drugs such as dobutamine or adenosine. The test is routinely carried out by general practitioners and local cardiologists.

Most individuals undergo cardiac stress testing without experiencing any problems. However, a considerable number of individuals develops serious cardiovascular adverse events such as myocardial infarction as a consequence of the test (see Pina, I. L., Balady, G. J., Hanson, P., et al. (1995) Guidelines for Clinical Exercise Testing Laboratories. Circulation, vol. 91, 912-921). These adverse events may even be fatal or near-fatal. Even non-fatal adverse events, such as non-fatal myocardial infarction, can have serious consequences, as the tissue of the muscle destroyed due to infarction can not be regenerated. Thus, a severe impairment of heart function and a disposition for further infarction or adverse events may remain and stress testing carries considerable risk for the individual.

One approach to make stress testing safer would be to perform the test exclusively in a clinical setting, and to have a physician trained in advanced cardiac life support ready for intervention. Indeed, such recommendations have been made (see Pina, I. L., Balady, G. J., Hanson, P., et al. (1995), Circulation, vol. 91, cited above). However, such a setting is not available everywhere and such precautions do not only increase the resources required for the test, but they may also cause undesirably long waiting lists and delay in scheduling an appointment for stress testing. Such a delay may itself carry a risk, as important diagnosis is delayed.

Currently, only individuals with a known history of relevant heart disease are referred to a clinical setting, because such individuals appear to be at risk of overstraining an already severely impaired organ during the test. Thus, there are still individuals undergoing stress testing in an unsafe environment who experience adverse events.

In some cases, parameter of heart function, e.g., echocardiogram, are measured before the test is carried out, in order to detect a relevant cardiac dysfunction. However, such measurements appear to be insufficient, as many cardiac dysfunctions remain undetected by echocardiography.

In some cases, levels of troponin T, creatine kinase (CK) or myoglobin are determined to exclude the presence of myocardial necrosis at the time of testing. However, these tests will detect only severe cardiac disease.

Foote et al. measured the levels of natriuretic peptides BNP and NT-proBNP in patients undergoing exercise stress testing before and after exercise stress testing (Foote, R. S., Pearlman, J. D., Siegel, A. H., Yeo, K-T. J. (2004). Detection of Exercise-Induced Ischemia by Changes in B-Type Natriuretic Peptides. Journal of the American College of Cardiology, vol. 44, no. 10., pp. 1980-1987). Foote et al. correlated the levels before and after the test with the presence or absence of myocardial ischemia during the stress test. However, only patients with already known coronary artery disease were enrolled in the study. Furthermore, only patients with resting levels of NT-proBNP and BNP within the normal range were enrolled. Thus the study did not allow a conclusion whether NT-proBNP and BNP allow stratifying individuals according to their risk of suffering from an adverse event during stress testing.

Weber et al. analyzed the levels of NT-proBNP in patients with stable angina pectoris before and after exercise stress testing (Weber, M., Dill, T., Arnold, R., Rau, M., et al. (2004). N-terminal B-type natriuretic peptide predicts extent of coronary artery disease and ischemia in patients with stable angina pectoris. Am Heart J, vol. 148, pp. 612-20). They found that within their patient sample, the levels of NT-proBNP were elevated in those patients with inducible ischemia as compared to those patients without inducible ischemia (396 pg/ml versus 160 pg/ml) during stress testing.

Sabatine et al. examined circulating BNP, NT-proBNP and NT-proANP levels before and after exercise stress testing (Sabatine, M. S., Morrow, D. A., de Lemos, J. A., Omland, T., Desai, M. Y., et al. (2004). Acute Changes in Circulating Natriuretic Peptide Levels in Relation to Myocardial Ischemia. Journal of the American College of Cardiology, vol. 44, no. 10, pp. 1988-95). They found that within their patient sample, the levels of NT-proBNP correlated with the no ischemia, mild-to-moderate ischemia and severe ischemia. Similar findings were made for BNP and NT-proANP.

The studies mentioned have focused on particular natriuretic peptides and the presence or absence of ischemia during stress testing. However, the levels found in these studies differed considerably, leaving it doubtful whether natriuretic peptides alone will allow a sufficiently reliable prediction of the appearing of ischemia during stress testing.

Thus, in the state of the art, there appears to be no method particularly suited to determine a risk whether an individual will suffer from a cardiovascular adverse event as a consequence of cardiac stress testing. Furthermore, there is a need for methods and uses to stratify individuals according to their risk of suffering from a cardiovascular adverse event as a consequence of cardiac stress testing.

SUMMARY OF THE INVENTION

The present invention relates to a method for determining a risk whether an individual will suffer from a cardiovascular adverse event as a consequence of cardiac stress testing, comprising the steps of (a) measuring, preferably in vitro, the level of placenta growth factor, wherein (b) if the level of the placenta growth factor is at least increased, then the individual is at least at risk of suffering from an adverse event as a consequence of cardiac stress testing. In a further embodiment, additionally another marker is measured, particularly a natriuretic peptide, most particularly NT-proBNP. The present invention allows stratifying patients according to the environment and conditions under which cardiac stress testing should be carried out.

DETAILED DESCRIPTION OF THE INVENTION

The object of the invention is attained by a method for determining a risk whether an individual will suffer from a cardiovascular adverse event as a consequence of cardiac stress testing, comprising the steps of
  measuring, preferably in vitro, the level of placenta growth factor or a variant thereof, wherein
  if the level of placenta growth factor or the variant thereof is at least increased, then the individual is at least at risk of suffering from an adverse event as a consequence of cardiac stress testing.

Furthermore, the object of the invention is attained by a method for determining a risk whether an individual will suffer from a cardiovascular adverse event as a consequence of cardiac stress testing, comprising the steps of
  measuring, preferably in vitro, the level of placenta growth factor or a variant thereof,
  measuring, preferably in vitro, the level of a natriuretic peptide or a variant thereof, wherein
  if the levels of both placenta growth factor and the natriuretic peptide, or a respective variant thereof, are at least increased, then the individual is at least at risk of suffering from an adverse event as a consequence of cardiac stress testing.

The methods according to the invention may also comprise the step of taking a body fluid or tissue sample of the individual.

According to the present invention, the level of placenta growth factor (PlGF) measured in an individual allows determining a risk of whether an individual is likely to suffer from an adverse event as a consequence of cardiac stress testing. More particularly, an increased level of PlGF indicates that the respective individual is at risk of suffering from an adverse event as a consequence of stress testing.

Thus, by measuring the level of PlGF, an individual elected for stress testing can be assigned to a given risk group, e.g., those individuals having a risk (increased or highly increased) of suffering from an adverse event as a consequence of cardiac stress testing and those individuals who have no increased risk of suffering from an adverse event.

In the context of the present invention, it has been realized that the level of PlGF provides information indicating a risk of suffering from an adverse event as a consequence of cardiac stress testing. It has been realized that, in contrast to the levels of natriuretic peptides, the level of PlGF is less influenced by high blood pressure or short-term changes such as physical exercise. Rather, the level of PlGF appears to indicate whether a more chronic cardiac disorder and/or more severe cardiac disorder is present in an individual. The present invention has realized that it is possible to take advantage of the information provided by the level of PlGF in the context of risk prediction.

In contrast, the levels of natriuretic peptides such as BNP, NT-proBNP, and NT-proANP appear to be more easily influenced by age and gender of an individual. The levels of these peptides can also be increased in case of high blood pressure. The levels can also be increased in case of cardiomyopathy other than perfusion defect, e.g., in the case of myocarditis or valve problems. It is also known that, e.g., BNP levels may increase after exercise in athletes and normal subjects in absence of myocardial ischemia. Thus, the level may be increased simply due to physical exercise shortly before the level is measured.

It should also be noted that there are patients with known coronary artery disease in whom the levels of NT-proBNP and BNP are within the normal range at rest (Foote et al. (2004), cited above). In this study, there was apparently a number of patients who showed myocardial ischemia during stress testing, although their levels of NT-proBNP and BNP might not have been associated with inducible myocardial ischemia according to the levels found relevant in other studies (Weber et al., (2004). Am Heart J, vol. 148. pp. 612-20 and Sabatine, et al. (2004). Journal of the American College of Cardiology, vol. 44, pp. 1988-95), both cited above).

Thus, measuring of BNP, NT-proBNP, and NT-proANP levels alone may result in a number of false positive and/or false negative results regarding inducible myocardial ischemia.

However, in the context of the present invention, it has been realized that the levels of PlGF and a natriuretic peptide can be measured in combination, simultaneously or non-simultaneously, in order to determine a risk whether an individual will suffer from a cardiovascular adverse event as a consequence of cardiac stress testing. It has been realized that the information provided by PlGF and a natriuretic peptide may complement each other advantageously and thus may provide an improved risk determination.

Advantageously, the present invention will allow assigning individuals to different settings of stress testing. E.g., individuals for whom the present invention indicates an increased risk or a highly increased risk will preferably be tested in a setting providing improved precautions for intervention in case of an adverse event. In such individuals also the level of strain may be lowered to reduce the risk of suffering from an adverse event.

In contrast, an individual for whom a method according to the present invention indicates no increased risk of suffering from an adverse event may undergo the test as planned, possibly at his local general practitioner. This may allow avoiding unnecessary long waiting lists at hospitals and it will allow the test to be performed as soon as possible. Of course, the decision on whether to test an individual at the local practitioner will be at the discretion of a physician who will base his decision on further information, e.g., the general health status, history of heart disease etc.

The invention takes advantage of certain biomarkers, in particular "biochemical markers" and "molecular markers". Biomarkers are known to the person skilled in the art. The term relates to molecules in an individual which are differentially present (i.e., present in increased or decreased levels) depending on presence or absence of a certain condition, disease, or complication. The terms "biochemical marker" and "molecular marker" are known to the person skilled in the art. In particular, biochemical or molecular markers are gene expression products which are differentially present (e.g., through increased or decreased level of expression or turnover) in presence or absence of a certain condition, disease, or complication. Usually, a molecular marker is defined as a nucleic acid (such as an mRNA), whereas a biochemical marker is a protein or peptide. The level of a suitable biomarker can indicate the presence or absence of a particular condition, disease, or risk, and thus allow diagnosis or determination of the condition, disease, or risk.

The present invention particularly takes advantage of PlGF and natriuretic peptides as biochemical markers.

Placenta growth factor (PlGF, also designated as PGF) is well-known to the person skilled in the art. It is a protein related to the vascular permeability factor (VPF or VEGF). The protein is 149 amino acids long and shares 53% identity with the platelet-derived growth factor-like region of VPF. PlGF appears to be involved in angiogenesis during development, certain periods of adult life, and tumorigenesis.

Natriuretic peptides according to the present invention comprise ANP-type and BNP-type peptides and variants thereof (see e.g. Bonow, R. O. (1996). New insights into the cardiac natriuretic peptides. Circulation 93: 1946-1950).

ANP-type peptides comprise pre-proANP, proANP, NT-proANP, and ANP.

BNP-type peptides comprise pre-proBNP, proBNP, NT-proBNP, and BNP.

The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP).

Preferred natriuretic peptides according to the present invention are NT-proANP, ANP, NT-proBNP, BNP, and variants thereof. ANP and BNP are the active hormones and have a shorter half-life than their respective inactive counterparts, NT-proANP and NT-proBNP. Therefore, depending on the time-course that is of interest, either measurement of the active or the inactive forms can be advantageous. The most preferred natriuretic peptides according to the present invention are NT-proBNP and variants thereof.

The term "variants" in this context relates to proteins or peptides substantially similar to said proteins or peptides. The term "substantially similar" is well understood by the person skilled in the art. In particular, a variant may be an isoform or allele which shows amino acid exchanges compared to the amino acid sequence of the most prevalent peptide isoform in the human population. Preferably, such a substantially similar peptide has a sequence similarity to the most prevalent isoform of the protein or peptide of at least 80%, preferably at least 85%, more preferably at least 90%, most preferably at least 95%. Substantially similar are also degradation products, e.g., proteolytic degradation products, which are still recognized by the diagnostic means or by ligands directed against the respective full-length protein or peptide. The term "variants" is also meant to relate to splice variants.

The term "variant" also relates to a post-translationally modified peptide such as glycosylated peptide. For example, N-glycosylation has been described for PlGF. A "variant" is also a peptide which has been modified after collection of the sample, for example by covalent or non-covalent attachment of a label, particularly a radioactive or fluorescent label, to the peptide.

Examples of particular variants and methods for their measurement are known are known (see e.g. Ala-Kopsala, M., Magga, J., Peuhkurinen, K. et al. (2004): Molecular heterogeneity has a major impact on the measurement of circulating N-terminal fragments of A-type and B-type natriuretic peptides. Clinical Chemistry, vol. 50(9), 1576-1588).

There are four isoforms of PlGF, designated PlGF-1 (PGF1), PlGF-2 (PGF2), PlGF-3 (PGF3) and PlGF-4 (PGF4). A preferred isoform in the context of the present invention is the PlGF-1, which is present in blood.

The invention also includes the measuring of different markers in combination, simultaneously or non-simultaneously. In particular, the present invention relates to measuring PlGF in combination with a natriuretic peptide, in particular NT-proBNP. According to the present invention any further markers may be measured in combination with PlGF. Examples for such markers include cardiac Troponin T and/or IMA (ischemia-modified albumin).

The term "cardiac stress testing" (which, in the context of the present invention, is also simply referred to as "stress testing") is known to the person skilled in the art. Cardiac stress testing is carried out to investigate how the cardiovascular system, particularly the heart, performs during exercise. In cardiac stress testing, the individual is subjected to cardiac strain while one or more diagnostic parameters of cardiovascular function are recorded.

The strain can be physical, particularly it can be physical exercise (known as "exercise stress test" or "exercise tolerance test"), e.g., it can be walking or running on a treadmill, riding a stationary bicycle (known as "bicycle ergometry"), or arm exercise testing (with arm ergometers). The strain can also be simulated by certain drugs administered to the individual (e.g., dipyridamole, dobutamine or adenosine). Typically, such drugs induce an increase in the frequency of heart beat und thus an increased strain. Preferably, such drugs are not cardiotoxic as such. Drug-induced strain may for example be used in disabled individuals. Preferably, the strain is of a nature which can be eliminated quickly in case of an adverse event. Therefore, e.g., increase of blood volume is a less preferred type of physical strain. As another example, the drug administered should have a short half-life in the body.

Commonly, the level of strain is increased during the test, i.e. while the one or more diagnostic parameters are recorded. For example, the steepness or speed of a treadmill is increased, the resistance of the bicycle drive is increased, or the dosage of the drug is increased.

The diagnostic parameters of cardiovascular function recorded during cardiac stress testing can be of any kind. It may include any of the following or a combination thereof: (a) the recording of an electrocardiogram (in particular for analysis of ST-segment changes, in particular elevation or lowering), (b) the recording of an echocardiogram, (c) the recording of radioisotope distribution, e.g., a thallium scintigram, (d) the recording of blood pressure, (e) the recording of breathing rate and/or heart rate, (f) ventilatory gas exchange analysis.

In the case of ST-segment changes, in particular elevation or lowering, chest pain with signs of myocardial ischemia, and/or unusual increase in blood pressure, the test should be discontinued.

A typical example of the stress test is the exercise EKG, which involves exercise testing (in this case typically riding a stationary bike or walking on a treadmill) while an electrocardiogram is being recorded.

Further details of stress testing are laid out in the above-mentioned article by Pina et al. (1995), which is incorporated herein in its entirety by reference. See particularly the sections superscribed "Equipment" and "Equipment calibration".

The present invention allows one to determine a risk (or to predict) whether an individual will suffer from a cardiovascular adverse event of any degree of severity as a consequence of cardiac stress testing. The term "cardiovascular adverse event" (or simply "adverse event") is known to the person skilled in the art. In the context of the present invention, the term "cardiovascular adverse event" (or simply "adverse event") relates to any kind of dysfunction of the heart or cardiovascular system. In particular, the term relates to any kind of reversible or non-reversible myocardial perfusion defect, reversible or non-reversible myocardial ischemia, ST-segment change (in particular elevation or lowering), angina pectoris, myocardial necrosis, myocardial infarction (MI, including ST-elevated MI or a non-ST-elevated MI), and stroke. Examples for severe adverse events include non-reversible myocardial perfusion defect or non-reversible myocardial ischemia, myocardial necrosis, myocardial infarction (MI, including ST-elevated MI or a non-ST-elevated MI), and stroke. Examples for very severe adverse events include myocardial infarction (MI, including ST-elevated MI or a non-ST-elevated MI), and stroke.

Particularly, the present invention relates to an adverse event occurring as a consequence of cardiac stress testing. It is known to the person skilled in the art under what circumstances an adverse event can be considered to occur "as a consequence" of stress testing. Such an adverse event is one which can be considered to be caused, elicited or precipitated by stress testing. A typical indicator that an adverse event has occurred as a consequence of stress testing is a close temporal relationship between stress testing and adverse event. Thus, an adverse event can particularly be considered to have occurred as a consequence of stress testing, if it occurs during stress testing or shortly (particularly within hours or a day) after stress testing. This may be indicated by the appearance of first symptoms of a later diagnosed dysfunction, e.g., a stroke should be considered to have occurred as a consequence of stress testing if first signs of numbness or paralysis appeared during or shortly after the test.

It has also been found, that the present invention provides diagnostic information in addition to the stress testing as such. For example, if a method according to the present invention indicates an increased or highly increased risk, then the individual may be subjected to further cardiac investigation, even if the stress testing itself did not reveal a cardiovascular dysfunction.

The individual according to the present invention can be any apparently healthy individual or patient elected for cardiac stress testing. An apparently healthy individual may be any individual who has not experienced symptoms of cardiovascular dysfunction. Such an individual may, e.g., be a person undergoing a regular health check-up (such as advised by many companies or governments for their employees). Further examples include athletes or pilots undergoing health testing.

In contrast, a patient is an individual who has experienced (or is currently experiencing) symptoms of a cardiovascular dysfunction, e.g., chest pain, shortness of breath (dyspnea), palpitation. Particularly, patient is an individual showing symptoms which would classify him as having cardiovascular dysfunction, according to the NYHA classification.

The NYHA classification is a functional classification system for cardiovascular dysfunctions according to the New York Heart Association (NYHA). Patients of Class I have no obvious symptoms of cardiovascular dysfunction. Physical activity is not limited, and ordinary physical activity does not cause undue fatigue, palpitation, or dyspnea (shortness of breath). Patients of class II have slight limitation of physical activity. They are comfortable at rest, but ordinary physical activity results in fatigue, palpitation, or dyspnea. Patients of class III show a marked limitation of physical activity. They are comfortable at rest, but less than ordinary activity causes fatigue, palpitation, or dyspnea. Patients of class IV are unable to carry out any physical activity without discomfort. They show symptoms of cardiac insufficiency at rest. If any physical activity is undertaken, discomfort is increased.

The present invention is particularly advantageous to patients which would be classified into NYHA class I or II. According to the state of the art, patients classified into NYHA class I or II may have been subjected to stress testing without a risk being expected. Advantageously, the invention allows detecting patients having a risk in these patient populations. Such patients should preferably undergo stress testing only under the conditions as laid out in this specification. The same is true for individuals showing no symptoms, i.e., apparently healthy individuals.

Methods and diagnostic means which can be used to determine the levels of the respective peptides are known to the person skilled in the art. These methods include microplate ELISA-based methods, fully-automated or robotic immunoassays (available for example on ELECSYS analyzers, Roche Diagnostics Gmbh), CBA (an enzymatic cobalt binding assay, available for example on Roche-Hitachi analyzers), and latex agglutination assays (available for example on Roche-Hitachi analyzers).

Furthermore, the person skilled in the art is familiar with different methods of measuring the level of a peptide or polypeptide. The term "level" relates to amount or concentration of a peptide or polypeptide in an individual or a sample taken from an individual.

The term "measuring" according to the present invention relates to determining the amount or concentration, preferably semi-quantitatively or quantitatively, protein, peptide, polypeptide, or other substance of interest. Proteins or peptides of particular interest in the context of the present invention are natriuretic peptides and PlGF. Measuring can be done directly or indirectly. Indirect measuring includes measuring of cellular responses, bound ligands, labels, or enzymatic reaction products.

In the context of the present invention, amount also relates to concentration. It is evident, that from the total amount of a substance of interest in a sample of known size, the concentration of the substance can be calculated, and vice versa.

Measuring can be done according to any method known in the art. Preferred methods are described in the following.

In a preferred embodiment, the method for measuring the level of a protein, peptide, or polypeptide of interest, comprises the steps of (a) contacting a cell capable of a cellular response to the protein, peptide or polypeptide with the protein, peptide or polypeptide for an adequate period of time, (b) measuring the cellular response.

In another preferred embodiment, the method for measuring the level of a protein, peptide or polypeptide of interest, comprises the steps of (a) contacting a protein, peptide or polypeptide with a suitable substrate for an adequate period of time, (b) measuring the amount of product.

In another preferred embodiment, the method for measuring the level of a peptide or polypeptide of interest, comprises the steps of (a) contacting a protein, peptide or polypeptide with a specifically binding ligand, (b) (optionally) removing non-bound ligand, (c) measuring the amount of bound ligand.

Preferably, the protein, peptide or polypeptide is contained in a sample, particularly a body fluid or tissue sample, and the amount of the protein, peptide or polypeptide in the sample is measured.

Proteins, peptides and polypeptides can be measured in tissue, cell, and body fluid samples, i.e., preferably in vitro. Preferably, the protein, peptide or polypeptide of interest is measured in a body fluid sample.

A tissue sample according to the present invention refers to any kind of tissue obtained from the dead or alive human or animal body. Tissue samples can be obtained by any method known to the person skilled in the art, for example by biopsy or curettage.

Body fluids according to the present invention may include blood, blood serum, blood plasma, lymph, cerebral liquor, saliva, and urine. Particularly, body fluids include blood, blood serum, blood plasma, and urine. One important example is the measurement in blood plasma or blood serum. Samples of body fluids can be obtained by any method known in the art.

Methods to obtain cell samples include directly preparing single cells or small cell groups, dissociating tissue (e.g. using trypsin), and separating cells from body fluids, e.g., by filtration or centrifugation. Cells according to the present invention comprise also platelets and other non-nuclear cells, e.g., erythrocytes.

If necessary, the samples may be further processed. Particularly, proteins, peptides or polypeptides may be purified from the sample according to methods known in the art, including filtration, centrifugation, or extraction methods such as chloroform-L/phenol extraction.

For measuring cellular responses, the sample or processed sample is added to a cell culture and an internal or external cellular response is measured. The cellular response may include the expression of a reporter gene or the secretion of a substance, e.g., a protein, peptide, polypeptide, or a small molecule.

Other preferred methods for measurement may include measuring the amount of a ligand binding specifically to the protein, peptide or polypeptide of interest. Binding according to the present invention includes both covalent and non-covalent binding.

A ligand according to the present invention can be any protein, peptide, polypeptide, nucleic acid, or other substance binding to the protein, peptide or polypeptide of interest. It is well known that proteins, peptides or polypeptides, if obtained or purified from the human or animal body, can be modified, e.g., by glycosylation. A suitable ligand according to the present invention may bind the protein, peptide or polypeptide exclusively or additionally via such sites.

Preferably, the ligand should bind specifically to the protein, peptide or polypeptide to be measured. "Specific binding" according to the present invention means that the ligand should not bind substantially to ("cross-react" with) another protein, peptide, polypeptide or substance present in the sample investigated. Preferably, the specifically bound protein or isoform should be bound with at least 3 times higher, more preferably at least 10 times higher and even more preferably at least 50 times higher affinity than any other relevant protein, peptide or polypeptide.

Non-specific binding may be tolerable, particularly if the investigated protein, peptide or polypeptide can still be distinguished and measured unequivocally, e.g., according to its size (such as on a Western Blot), or by its relatively higher abundance in the sample.

Binding of the ligand can be measured by any method known in the art. Preferably, the method is semi-quantitative or quantitative. Suitable methods are described in the following.

First, binding of a ligand may be measured directly, e.g., by NMR or surface plasmon resonance.

Second, if the ligand also serves as a substrate of an enzymatic activity of the peptide or polypeptide of interest, an enzymatic reaction product may be measured (e.g., the amount of a protease can be measured by measuring the amount of cleaved substrate, e.g., on a Western Blot).

For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for a detectable, preferably measurable amount of product to be produced. Instead of measuring the amount of product, the time necessary for appearance of a given (e.g., detectable) amount of product can be measured.

Third, the ligand may be coupled covalently or non-covalently to a label allowing detection and measurement of the ligand.

Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.)

The ligand or substrate may also be "tagged" with one or more tags as known in the art. Such tags may then be targets for higher order ligands. Suitable tags include biotin, digoxigenin, his-tag, glutathione-S-transferase, FLAG, GFP, myc-tag, influenza A virus haemagglutinin (HA), maltose binding protein, and the like. In the case of a peptide or polypeptide, the tag is preferably at the N-terminus and/or C-terminus.

Suitable labels are any labels detectable by an appropriate detection method. Typical labels include gold particles, latex beads, acridan ester, luminol, ruthenium, enzymatically active labels, radioactive labels, magnetic labels (e.g., "magnetic beads", including paramagnetic and superparamagnetic labels), and fluorescent labels.

Enzymatically active labels include, e.g., horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star (Amersham Biosciences), ECF (Amersham Biosciences). A suitable enzyme-substrate combination may result in a colored reaction product, fluorescence or chemiluminescence, which can be measured according to methods known in the art (e.g. using a light-sensitive film or a suitable camera system). As for measuring the enzymatic reaction, the criteria given above apply analogously.

Typical fluorescent labels include fluorescent proteins (such as GFP and its derivatives), Cy3, Cy5, Texas Red, Fluorescein, and the Alexa dyes (e.g., Alexa 568). Further fluorescent labels are available, e.g., from Molecular Probes (Oregon). Also the use of quantum dots as fluorescent labels is contemplated.

Typical radioactive labels include 35S, 125I, 32P, 33P and the like. A radioactive label can be detected by any method known and appropriate, e.g., a light-sensitive film or a phosphor imager.

Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immunoassay (DELFIA), scintillation proximity assay (SPA), turbidimetry, nephelometry, latex-enhanced turbidimetry or nephelometry, solid phase immune tests, and mass spectrometry such as SELDI-TOF, MALDI-TOF, or capillary electrophoresis-mass spectrometry (CE-MS). Further methods known in the art (such as gel electrophoresis, 2D gel electrophoresis, SDS polyacrylamide gel electrophoresis (SDS-PAGE), Western Blotting), can be used alone or in combination with labeling or other detection methods as described above.

Preferred ligands include antibodies, nucleic acids, proteins, peptides or polypeptides, and aptamers, e.g., nucleic acid or peptide aptamers. Methods to such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, proteins, peptides or polypeptides. These derivatives can then be tested for binding according to screening procedures known in the art, e.g., phage display.

The term "antibody" as used herein includes both polyclonal and monoclonal antibodies, as well as any modifications or fragments thereof, such as Fv, Fab and $F(ab)_2$ fragments that are capable of binding antigen or hapten.

In another preferred embodiment, the ligand, preferably chosen from the group consisting of nucleic acids, proteins, peptides, polypeptides, more preferably from the group consisting of nucleic acids, antibodies, or aptamers, is present on an array.

Said array contains at least one additional ligand, which may be directed against a protein, peptide or polypeptide interest. Said additional ligand may also be directed against a protein, peptide, or polypeptide of no particular interest in the context of the present invention. Preferably, ligands for at least three, preferably at least five, more preferably at least eight proteins, peptides or polypeptides of interest in the context of the present invention are contained on the array.

According to the present invention, the term "array" refers to a solid-phase or gel-like carrier upon which at least two compounds are attached or bound in one-, two- or three-dimensional arrangement. Such arrays (including "gene chips", "protein chips", antibody arrays and the like) are generally known to the person skilled in the art and typically generated on glass microscope slides, specially coated glass slides such as polycation-, nitrocellulose- or biotin-coated slides, cover slips, and membranes such as, for example, membranes based on nitrocellulose or nylon.

The array may include a bound ligand or at least two cells expressing each at least one ligand.

It is also contemplated to use "suspension arrays" as arrays according to the present invention (Nolan J P, Sklar L A. (2002). Suspension array technology: evolution of the flat-array paradigm. Trends Biotechnol. 20(1):9-12). In such suspension arrays, the carrier, e.g., a microbead or microsphere, is present in suspension. The array consists of different microbeads or microspheres, possibly labeled, carrying different ligands.

The invention further relates to a method of producing arrays as defined above, wherein at least one ligand is bound to the carrier material in addition to other ligands.

Methods of producing such arrays, for example based on solid-phase chemistry and photo-labile protective groups, are generally known (U.S. Pat. No. 5,744,305). Such arrays can also be brought into contact with substances or substance libraries and tested for interaction, for example for binding or change of confirmation. Therefore, arrays comprising a peptide or polypeptide as defined above may be used for identifying ligands binding specifically to said peptides or polypeptides.

The present invention also relates to a kit comprising a means or an agent for measuring PIGF. Optionally, the kit may also comprise means or agents for measuring a natriuretic peptide or any other biomarker mentioned in this specification (e.g., Troponin T, IMA, creatine kinase, myoglobin, etc.). Such means or agent may be any suitable means or agent known to the person skilled in the art. Examples for such means or agents as well as methods for their use have been given in this specification. For example, a suitable agent may be any kind of ligand or antibody specific for measuring PIGF, natriuretic peptide, or other biomarker, respectively. The kit may also comprise any other components deemed appropriate in the context of measuring the level(s) of the respective biomarkers, such as suitable buffers, filters, etc.

Optionally, the kit may additionally comprise a user's manual for interpreting the results of any measurement(s) with respect to determining the risk of an individual of suffering from a cardiovascular adverse event as a consequence of cardiac stress testing. Particularly, such manual may include information about what measured level corresponds to what kind of risk group. This is outlined in detail elsewhere in this specification. Additionally, such user's manual may provide instructions about correctly using the components of the kit for measuring the level(s) of the respective biomarkers.

The present invention also relates to the use of said kit for determining a risk whether an individual will suffer from a cardiovascular adverse event as a consequence of cardiac stress testing. The present invention also relates to the use of said kit in any of the methods according to the present invention for determining a risk whether an individual will suffer from a cardiovascular adverse event as a consequence of cardiac stress testing According to the present invention, the measured level of PIGF indicates whether an individual will suffer from a cardiovascular adverse event as a consequence of cardiac stress testing. The same applies analogously if the levels of PIGF and a natriuretic peptide are measured in combination. The terms used in this context, i.e., "non-increased level", "increased level", and "highly increased level" are known to the person skilled in the art. The person skilled in the art is able to determine actual values for the relevant biochemical markers which correspond to these levels.

For example, the levels may be assigned according to percentiles of the levels observed in a representative sample of apparently healthy individuals below an age of 50 years (preferably, the sample comprises at least 100, more preferably at least 500, most preferably at least 1000 individuals). E.g., a non-increased level may correspond to the maximum level observed in the 97.5% percentile.

Alternatively, the levels may be determined as "normal ranges" as known in the state of the art. The levels may also be determined or further refined by studies performed on individuals undergoing stress testing and correlating any adverse events with the levels observed in the individuals. Such studies may also allow tailoring the levels according to certain patient sub-groups, e.g., patients with known coronary artery disease, elderly patients, or apparently healthy individuals. Guidance on how such studies may be carried out can also be obtained from the Examples included in this specification.

The value of the levels considered as "increased" or "highly increased" may also be chosen according to the desired sensitivity or specificity (stringency) of exclusion. The higher the desired sensitivity, the lower is the specificity of exclusion and vice versa. In the above example, the higher the percentile chosen to determine each level, the more stringent is the exclusion criterion, i.e. less individuals would be considered "risk individuals" or excluded from stress testing.

Below, examples for actual levels are provided for PIGF and NT-proBNP. It is evident, that the levels given below can serve only as a first classification of the risk of an individual. For example, the risk may also dependent on the spare pumping capacity of heart of a particular individual or on the general health status of the individual.

In this example, concerning PlGF, a plasma level of less than 10 pg/ml is considered a non-increased level. Furthermore, a plasma level of 10-20 pg/ml is considered an increased level. Furthermore, a plasma level of more than 20 pg/ml is considered a highly increased level.

In this example, concerning NT-proBNP, a plasma level of less than 125 pg/ml is considered a non-increased level. Furthermore, a plasma level of 125-300 pg/ml is considered an increased level. Furthermore, a plasma level of more than 300 pg/ml is considered a highly increased level.

Both for PlGF and NT-proBNP, serum levels would be comparable to plasma levels. Corresponding levels, e.g., in whole blood or other samples can be determined by the person skilled in the art.

The method according to the present invention also allows determining the risk of an individual of suffering from an adverse event during stress testing. According to the present invention, the term "risk" relates to the probability of a particular incident, more particularly an adverse event, to take place. The grade of risk can be non-increased, increased, or highly increased. "Non-increased risk" means that there is apparently no risk of suffering from a cardiovascular adverse event as a consequence of stress testing.

The degree of risk is associated with the levels of PlGF (or PlGF and a natriuretic peptide). A non-increased level PlGF indicates no increased risk, an increased level of PlGF indicates an increased risk, and a highly increased level of PlGF indicates a highly increased risk. In the case of combined measurement of PlGF and a natriuretic peptide the risks are calculated analogously. However, it may be considered sufficient to indicate a highly increased risk if only one of the markers, i.e. either PlGF or natriuretic peptide, is highly increased, whereas the level of the respective other marker is merely increased.

If the level of PlGF is non-increased, the stress test may be carried out as planned, e.g., at a local cardiologist's practice, preferably taking the usual recommended precautions. In this case, it may also be tolerable to schedule the test not immediately. The same applies in the case of combined measurement if the levels of both PlGF and natriuretic peptide are non-increased.

As already mentioned, if the methods according to the present invention indicate an increased or highly increased risk, it will preferably have consequences for the stress testing.

In a first aspect, if the risk is increased or highly increased, stress testing should be performed without undue delay. Particularly in the case of a highly increased risk, the test should be carried out immediately in order to obtain necessary diagnostic information.

In a second aspect, if the risk is increased or highly increased, stress testing should be performed in a safe hospital setting, e.g., with emergency trained medical staff readily available and/or using an automatic arrhythmia detector. Particularly in the case of a highly increased risk, the test should be carried out in a hospital unit with improved possibilities for intervention such as percutaneous coronary intervention (PCI) and surgical intervention possibilities.

In a third aspect, if the risk is increased or highly increased, the stress testing is preferably carried out at a limited level of strain, particularly in the case of highly increased risk.

The following examples illustrate the invention.

EXAMPLE 1

Measurement of NT-proBNP

NT-proBNP was determined by an electrochemiluminescence immunoassay (ELECSYS proBNP sandwich immunoassay; Roche Diagnostics, Mannheim, Germany) on ELECSYS 2010. The assay works according to the electrochemiluminescence sandwich immunoassay principle. In a first step, the biotin-labeled IgG (1-21) capture antibody, the ruthenium-labeled F(ab')2 (39-50) signal antibody and 20 microliters of sample are incubated at 37° C. for 9 minutes. Afterwards, streptavidin-coated magnetic microparticles are added and the mixture is incubated for additional 9 minutes. After the second incubation, the reaction mixture is transferred to the measuring cell of the system where the beads are magnetically captured onto the surface of an electrode. Unbound label is removed by washing the measuring cell with buffer.

In the last step, voltage is applied to the electrode in the presence of a tri-propylamine containing buffer and the resulting electrochemiluminescent signal is recorded by a photomultiplier. All reagents and samples are handled fully automatically by the ELECSYS instrument. Results are determined via a calibration curve which is instrument-specifically generated by 2-point calibration and a master curve provided via the reagent barcode. The test was performed according to the instructions of the manufacturer.

EXAMPLE 2

Analysis

Blood for hormone analysis was sampled in EDTA-tubes containing 5000 U aprotinine (Trasylol, Beyer, Germany) and Lithium-Heparin-tubes (for clinical chemistry), as appropriate. Blood and urine samples were immediately spun for 10 min. at 3400 rpm at 4° C. Supernatants were stored at −80° C. until analysis.

Determination of PlGF:

Placental Growth Factor (PlGF) was measured by an enzyme-linked immunosorbent microtiter plate assay (R&D Systems, Wiesbaden, Germany). Total imprecision (expressed as coefficient of variation) for PlGF was 7.3%. The PlGF test recognizes the isoform PlGF-1 but has at least 50% cross-reactivity to PlGF-2.

Determination of NT-proBNP:

NT-proBNP was determined by an electrochemiluminescence immunoassay (ELECSYS proBNP sandwich immunoassay; Roche Diagnostics, Basel, Switzerland) on ELECSYS 2010 (Mueller, T., Gegenhuber, A. (2003). Comparison of the Biomedica NT-proBNP enzyme immunoassay and the Roche NT-proBNP chemiluminescence immunoassay: implications for the prediction of symptomatic and asymptomatic structural heart disease. Clin. Chem. 49:976-9), see also Example 1. The mean intra-assay variance was 4.3% (range: 2.7 to 5.9% for plasma samples with a concentration between 7.6 to 2732 pmol *1-1 with an interassay variance of 3.2%. The lower detection limit was 0.6 pmol *1-1.

Determination of NT-proANP:

NT-pro ANP was measured using a competitive-binding radioimmunoassay with magnetic solid phase technique using a rabbit-anti-rat proANP polyclonal serum, human proANP (1-30) from Peninsula Lab (Bachem Ltd, St. Helene, UK) and iodined proANP (1-30) purified by HPLC for radiolabeling. In order to achieve high sensitivity and good precision, Dynabeads M280 with sheep-anti-rabbit IgG (Dynal Biotech, Oslo, Norway) as solid phase and second antibody were used. The minimal detectable concentration is 105 pg/ml, the coefficient of variation is 7.5% at 1490 pg/ml, 3.7% at 4077 pg/ml and 3.4% at 8730 pg/ml respectively.

Determination of IMA:

Ischemia-modified albumin was measured with the Albumin Cobalt Binding (ACB) Test. The ACB Test (ISCHEMIA Technologies, inc, Colorado, USA) is configured to run on the ROCHE/HITACHI MODULAR P instrument. Intra- and inter-assay precision were determined between CV 2.2-4.1% and CV 4.3-7.1%, respectively.

Determination of Cardiac Troponin T (cTnT):

cTnT was measured quantitatively using a one-step EIA based on electrochemiluminescence technology (3rd generation cTnT, ELECSYS 2010, Roche Diagnostics, Mannheim, Germany). The lower detection limit of this assay is 0.01 µg/l with a recommended diagnostic threshold of 0.03 µg/l. The inter-assay coefficients of variation (between day imprecision data set of at least II runs) at different concentrations were 20% for 0.015 µg/L, 10% for 0.03 µg/l and 5% for 0.08 µg/l.

EXAMPLE 3

A total of 195 consecutive patients who underwent thallium scintigraphy for suspected significant coronary artery disease were studied.

Patients underwent bicycle exercise testing using a standard exercise protocol or received pharmacological testing with dipyridamol at a dose of 42.72 mg (±7.61) using a standard protocol. Allocation to dynamic or pharmacological exercise testing was left at the discretion of the nuclear cardiologist. The protocol was approved by the local ethical committee of the University of Heidelberg, and all patients gave informed consent prior to inclusion.

Single-photon emission computed tomography myocardial perfusion (SPECT) imaging was carried out as follows: Thallium was administered at peak stress, and imaging was performed immediately thereafter. Four hours later, a repeat imaging was performed. A 17 segment myocardial model was used for semiquantitative analysis. Two nuclear cardiologists unaware of biomarker results categorized the images as having no perfusion defects, only reversible perfusion defects, and fixed perfusion defects. Patients with a combination of reversible, partially reversible, and fixed perfusion defects were excluded from primary analysis and evaluated separately.

Blood samples were obtained immediately before, immediately after, and 4 hours after stress testing. A very late blood sample was collected in all patients with a third scan (redistribution scan) on the next day (n=20). Blood samples were placed on ice and processed within 30 minutes. Plasma aliquots were stored at −80° C. and thawed before analysis.

Statistical Analysis was carried out as follows: Plasma concentrations of cTnT, N-terminal atrial natriuretic peptide (NT-pro ANP), N-terminal B-type natriuretic peptide (NT-pro BNP), Placental Growth Factor (PIGF), ischemia-modified albumin (IMA) are described as median values with the corresponding interquartile range, or as mean values with the corresponding standard error. The baseline characteristics of patient groups were compared using the Mann-Whitney U test or Student's t-test for continuous variables and the chi-square test for categorical variables. The Kolmogorov-Smirnov test was used to test for normal distribution. For all analyses, a value of $P<0.05$ was regarded as statistically significant. All statistical analyses were carried out using the SPSS software package version 12.01 (SPSS Inc, Chicago, Ill., USA).

Baseline characteristics: Among the entire cohort of 195 study participants 24 (12%) patients had reversible perfusion defects and 62 (32%) had no perfusion defects. 109 (56%) patients had either fixed perfusion defects or a combination of fixed and reversible perfusion defects. All data and analyses on biomarkers presented in the following are confined to the 24 patients with reversible perfusion defects and to the 62 patients without fixed or reversible perfusion defects. Patients with reversible perfusion defects had more often a history of coronary artery disease, previous MI (myocardial infarction), prior PCI (percutaneous coronary intervention) or CABG (coronary artery by pass graft) (83.3 vs 56.5%, p=0.02) and underwent more frequently percutaneous coronary interventions (12.5% vs 1.6%, p=0.04) after thallium scintigraphy. The total dose of dipyridamol was significantly higher in patients with inducible myocardial ischemia (48.5 vs 38.8 mg, p=0.002). All other parameters were comparable in both groups. The detailed baseline characteristics of all 195 study participants as well as of those with a reversible perfusion defect (ischemia group) and those without a reversible perfusion defect (non-ischemia group) are displayed in details in Table 1.

Of the final study group, 52 patients underwent bicycle exercise testing and 34 patients received dipyridamol stress testing. Among patients undergoing dynamic exercise testing, mean exercise duration (8.75±3.32 minutes vs 7.74±0.42 minutes, p=0.23) or peak work load (125±9 watts vs 109±5 watts, p=0.15) was not different in patients with reversible perfusion defects as compared to patients without perfusion defects. Total duration of dipyridamol infusion was comparable in both groups (5.0±0.0 minutes vs 5.21±0.21 minutes, p=0.85). Detailed information on differences between pharmacological or dynamic stress test are displayed in Table 2. Angina pectoris was experienced by 4 of 24 patients (16.7%) in the reversible ischemia group and in 8 of 62 patients (12.9%) in the group without perfusion defects.

Plasma levels of biomarkers were measured before, after a mean of 17.85±11.14 minutes, and after a mean of 4.05±0.64 hours. A fourth blood sample was collected on the day after thallium scintigraphy (mean 24.12±1.51 hours). The small number of patients (n=19) did not allow a statistically powered analysis for the fourth sample.

Placental Growth Factor:

Baseline levels of PIGF were found to be 15.15 pg/ml in patients who developed reversible perfusion defects as compared to 11.35 pg/ml in patients without (see Table 3 for details).

Cardiac Troponin T:

Plasma concentrations of cTnT at baseline were below the lower limit of detection (0.01 µg/L) in all but 7 patients and did not increase significantly after stress testing. Increased plasma levels of cTnT in these 7 patients were related to prior acute myocardial infarction within 14 days before stress testing. Cardiac troponin concentrations did not increase at 18 minutes or at 4 hours after exercise testing and were comparable at all time points in patients without perfusion defects and in patients with reversible perfusion defects. Relative changes of cardiac biomarkers before and after exercise-induced ischemia are shown in Table 3.

NT-pro BNP, NT-pro ANP

Baseline levels of NT-pro BNP and NT-pro ANP were significantly higher in patients who later developed reversible perfusion defects. However, blood levels of NT-pro BNP and NT-pro ANP did not rise significantly at 18 minutes or at 4 hours in patients with or without perfusion defects.

Ischemia-modified albumin

Plasma concentrations of IMA were comparable at baseline in patients without perfusion defects and in patients with reversible perfusion defects. After a transient drop at 18 minutes IMA raised significantly at 4 hours (p=0.001 for patients with no perfusion defects, p 0.013 for patients with reversible perfusion defect). However, an increase of IMA level occurred in patients with and without reversible perfusion defects and was exclusively related to patients who received exercise stress test as compared to pharmacological stress test.

Change of biomarker levels according to the type of exercise test: The baseline concentrations of all biomarkers were comparable in patients undergoing dynamic and in those undergoing pharmacological stress (Table 4). Concentrations did not change significantly immediately after stress or at 4 hours, except for IMA.

TABLE 1

Clinical characteristics of study population

|  | All n = 195 | Non-ischemia n = 62 (32%) | Reversible ischemia n = 24 (12%) | P |
|---|---|---|---|---|
| Men n (%) | 137 (70%) | 31 (50%) | 16 (67%) | 0.16 |
| Age (years) | 67.65 (± 9.78) | 67.48 (± 2.08) | 70.21 (± 1.41) | 0.26 |
| BMI | 28 | 27 | 30 | 0.12 |
| Current smoker | 54 (28%) | 17 (27%) | 7 (29%) | 0.87 |
| Hypertension | 166 (85%) | 49 (79%) | 18 (75%) | 0.69 |
| Hypercholesterolemia | 146 (75%) | 43 (69%) | 15 (63%) | 0.92 |
| Diabetes mellitus | 63 (32%) | 15 (24%) | 6 (25%) | 0.92 |
| History of CAD | 155 (79%) | 35 (56%) | 20 (83%) | 0.02 |
| History of MI | 52 (27%) | 5 (8%) | 5 (21%) | 0.10 |
| History of CABG | 34 (17%) | 7 (11%) | 4 (17%) | 0.50 |

Abbreviations:
BMI: body mass index;
MI: myocardial infarction;
CAD: coronary artery disease;
CABG: coronary artery bypass graft;

TABLE 2

Stress test procedures

|  | All n = 195 | Non-ischemia n = 62 | Reversible ischemia n = 24 | P |
|---|---|---|---|---|
| Indication for stress test: |  |  |  |  |
| Symptoms alone | 105 (54%) | 8 (13%) | 4 (17%) | 0.18 |
| Progress of known CAD | 85 (44%) | 3 (37%) | 1 (5%) | 0.46 |
| Angiography before exam | 146 (75%) | 38 (61%) | 18 (75%) | 0.23 |
| Type of stress test: |  |  |  |  |
| Bicycle exercise | 116 (59%) | 38 (61%) | 14 (58%) | 0.08 |
| Dipyridamol | 79 (41%) | 24 (39%) | 10 (42%) | 0.08 |
| Test parameters: Duration (min): |  |  |  |  |
| Bicycle exercise | 8.37 (± 2.89) | 7.74 (± 0.42) | 8.75 (± 3.32) | 0.23 |
| Dipyridamol | 5.13 (± 0.79) | 5.21 (± 0.21) | 5.00 (± 0.00) | 0.85 |
| Work load: |  |  |  |  |
| Peak watts (bicycle) | 117 (± 32) | 109 (± 5) | 125 (± 9) | 0.15 |
| Total dose (mg Dipyridamol) | 42.72 (± 7.61) | 38.79 (± 1.38) | 48.50 (± 7.03) | 0.002 |
| Clinical findings: |  |  |  |  |
| Inducible angina | 30 (15%) | 8 (13%) | 4 (17%) | 0.65 |
| ST-depression >0.15 | 35 (18%) | 10 (16%) | 5 (21%) | 0.61 |

Abbreviations:
CAD: coronary artery disease;
CABG: coronary artery bypass graft;
PCI: percutaneous coronary intervention;

TABLE 3

Relative changes of cardiac biomarkers before and after exercise-induced ischemia

|  | Baseline | After 18 minutes | After 4 hours |
|---|---|---|---|
| cTnT (µg/l) |  |  |  |
| No perfusion defect | 0.01 (0.01/0.01) | 0.01 (0.01/0.01) | 0.01 (0.01/0.01) |
| Reversible perfusion defect | 0.01 (0.01/0.01) | 0.01 (0.01/0.01) | 0.01 (0.01/0.01) |
| NT-pro BNP (pg/ml) |  |  |  |
| No perfusion defect | 139.00 (58.25/367.01) | 161.00 (70.78/417.99) | 168.95 (70.99/447.74) |
| Reversible perfusion defect | 327.45* (120.50/972.85) | 311.86 (126.66/816.41) | 318.54 (142.58/1027.50) |
| NT-pro ANP (pg/ml) |  |  |  |
| No perfusion defect | 732.5 (470.0/1220.0) | 810.5 (522.0/1295.0) | 768.0 (490.3/1137.5) |
| Reversible perfusion defect | 1470.0* (694.0/1910.0) | 1410.0 (782.0/2040.0) | 1345.0 (924.0/1770.0) |
| IMA (U/ml) |  |  |  |
| No perfusion defect | 84.0[#1] (80.0/93.0) | 81.5[#2] (69.0/91.0) | 93.5 (84.0/106.0) |
| Reversible perfusion defect | 82.5[#3] (78.0/90.0) | 71.0[#4] (67.5/89.0) | 96.5 (88.5/100.5) |

TABLE 3-continued

Relative changes of cardiac biomarkers before
and after exercise-induced ischemia

|  | Baseline | After 18 minutes | After 4 hours |
|---|---|---|---|
| PlGF (ng/L) | | | |
| No perfusion defect | 11.35 (5.98/20.25) | 12.50 (6.77/23.50) | 14.90 (6.40/23.40) |
| Reversible perfusion defect | 15.15 (9.78/24.26) | 16.08 (10.66/24.65) | 17.99 (11.18/23.39) |

Abbreviations:
cTNT: cardiac troponin T;
NT-pro BNP: N-terminal pro-B-type natriuretic peptide;
NT-pro ANP: N-terminal atrial natriuretic peptide;
IMA: ischemia modified albumin; PlGF: Placental Growth Factor.
*$p<0.05$ for comparison between reversible perfusion defect versus no perfusion defect. All data are given as medians with corresponding 25th and 75th percentiles (Q1/Q3).
[#1] $p = 0.0070$ from baseline to 4 hours,
[#2] $p < 0.0001$ from 18 min to 4 hours
[#3] $p = 0.0351$ from baseline to 4 hours,
[#4] $p = 0.0130$ from 18 min to 4 hours

TABLE 4

Markers of ischemia according to type of stress

|  | Baseline | After 18 minutes | After 4 hours |
|---|---|---|---|
| cTnT (µg/l) | | | |
| Pharmacologic | 0.01 (0.01/0.01) | 0.01 (0.01/0.01) | 0.01 (0.01/0.01) |
| Dynamic | 0.01 (0.01/0.01) | 0.01 (0.01/0.01) | 0.01 (0.01/0.01) |
| NT-pro BNP (pg/ml) | | | |
| Pharmacologic | 162.3 (70.2/784.5) | 200.1 (74.8/766.5) | 245.3 (97.0/813.2) |
| Dynamic | 148.9 (106.4/355.0) | 161.0 (115.1/366.8) | 169.0 (116.8/422.1) |
| NT-pro ANP (pg/ml) | | | |
| Pharmacologic | 731.0 (562.3/1422.5) | 810.5 (525.0/1400.0) | 797.0 (557.0/1425.0) |
| Dynamic | 923.0 (609.3/1672.5) | 900.0 (681.5/1455.0) | 908.5 (611.5/1345.0) |
| IMA (U/ml) | | | |
| Pharmacologic | 89.0[#1] (83.0/97.0) | 97.0[#2] (89.0/106.0) | 99.0 (85.0/108.0) |
| Dynamic | 83.0[#3] (78.5/90.0) | 75.0[#4] (66.0/82.5) | 93.0 (86.0/100.5) |
| PlGF (ng/L) | | | |
| Pharmacologic | 11.35 (8.55/21.25) | 16.30 (8.23/25.62) | 16.80 (7.47/23.35) |
| Dynamic | 13.54 (7.00/22.57) | 13.25 (8.35/23.48) | 14.60 (6.72/22.96) |

Abbreviations:
cTNT: cardiac troponin T;
NT-pro BNP: N-terminal pro-B-type natriuretic peptide;
NT-pro ANP: N-terminal atrial natriuretic peptide;
IMA: ischemia modified albumin;
PlGF: Placental Growth Factor.
All data are given as medians with corresponding 25th and 75th percentiles (Q1/Q3).
[#1] $p = 0.2507$ from baseline to 4 hours,
[#2] $p = 0.7304$ from 18 min to 4 hours
[#3] $p = 0.0008$ from baseline to 4 hours,
[#4] $p < 0.0001$ from 18 min to 4 hours

EXAMPLE 4

A 45 year old man who smokes 40 cigarettes per day on a regular basis presents to his physician for stress testing. In a blood analysis blood chemistry is within the normal range including CK and CKMB.

However, PlGF is found to be 16 pg/ml and NT-proBNP 260 pg/ml. Patient has no complaints, blood pressure is 140 to 98 mm/hg. On request he reports that he does not sports. Based on the result of PlGF and NT-proBNP, stress testing is not carried out at his physician's office, but he is referred to a cardiologist. The ECG is not abnormal and echocardiography does not show any abnormalities. In the cardiologist office he is submitted to stress testing resulted in chest-pain at 200 W. This is associated with a significant increase in blood pressure. In addition, arrhythmia occurs. Due to the relatively safe environment and experienced staff at the cardiologist's office, the adverse events remain under control and the patient is sent for further evaluation to the hospital where a coronary angiography reveals a stenosis of the left coronary artery.

EXAMPLE 5

A 62 year old woman who does regular sports presents to her physician because of repeated chest-pain sometimes related to exercise but also at times unrelated to exercise. She does not smoke. Her blood chemistry levels are within the normal range. PlGF is found to be 8 pg/ml. For confirmation, NT-proBNP is measured additionally and found to be 59 pg/ml. Blood pressure is 140 to 70 mm/hg. An ECG shows no abnormalities. In light of the low levels of PlGF and NT-proBNP, a cardiac stress test is considered safe to be performed in the physician's office. The stress test shows no abnormalities. The patient is referred to a pulmonologist for further assessment of her repeatedly occurring chest-pain as there is no evidence for coronary artery disease.

What is claimed is:

1. A method for determining a risk of experiencing a cardiovascular adverse event as a consequence of cardiac stress testing in an apparently healthy individual or an individual classified into New York Heart Association (NYHA) classes I or II by assessing perfusion impairment, the method comprising the steps of
    measuring in a plasma sample from the individual a level of placenta growth factor (PlGf) and
    determining the risk by comparing the measured level of PlGF to a standard plasma level of PlGF equal to 10 pg/ml whereby if a measured level corresponds to a
    plasma level of PlGF greater than 10 pg/ml, the risk is increased.

2. The method of claim 1 wherein if the measured level corresponds to a plasma level of PlGF greater than 20 pg/ml, the risk is highly increased.

3. The method of claim 1 further comprising the step of measuring a level of a natriuretic peptide in a sample from the individual and augmenting determination of the risk by comparing the measured level of natriuretic peptide to a standard level of natriuretic peptide.

4. The method of claim 3 wherein the natriuretic peptide is selected from the group consisting of pre-proANP, proANP, NT-proANP, ANP, pre-proBNP, proBNP, NT-proBNP, and BNP.

5. The method of claim 4 wherein the natriuretic peptide is NT-proBNP.

6. The method of claim 5 whereby if a measured level of NT-proBNP corresponds to a plasma level of NT-proBNP greater than 125 pg/ml, the risk is increased.

7. The method of claim 5 whereby if a measured level of NT-proBNP corresponds to a plasma level of NT-proBNP greater than 300 pg/ml, the risk is highly increased.

8. The method of claim 1 further comprising the steps of measuring a level of a marker selected from the group consisting of troponin T, ischemia-modified albumin (IMA), creatine kinase, and myoglobin in a sample from the individual and comparing the measured level of the marker to a standard level of the marker.

9. The method of claim 1 wherein the adverse event is selected from the group consisting of reversible myocardial ischemia, non-reversible myocardial ischemia, ST-segment change, angina pectoris, myocardial necrosis, myocardial infarction, and stroke.

* * * * *